United States Patent [19]

Würmli et al.

[11] 4,410,331
[45] Oct. 18, 1983

[54] CONDENSATION PRODUCTS CONTAINING SULPHONIC ACID GROUPS: ADDITIVES FOR DYEING SYNTHETIC POLYAMIDE

[75] Inventors: Albert Würmli, Riehen; Hans U. Berendt, Allschwil, both of Switzerland

[73] Assignee: Ciba-Geigy Corporation, Ardsley, N.Y.

[21] Appl. No.: 292,546

[22] Filed: Aug. 13, 1981

Related U.S. Application Data

[60] Division of Ser. No. 167,578, Jul. 11, 1980, Pat. No. 4,322,372, which is a continuation of Ser. No. 937,367, Aug. 28, 1978, abandoned, which is a continuation of Ser. No. 769,376, Feb. 16, 1977, abandoned, which is a continuation of Ser. No. 659,309, Feb. 19, 1976, abandoned, which is a continuation of Ser. No. 365,886, Jun. 1, 1973, abandoned.

[30] Foreign Application Priority Data

Jun. 15, 1972 [CH] Switzerland ............... 8980/72

[51] Int. Cl.³ ............... C07C 139/00; C07C 143/42; D06P 1/84
[52] U.S. Cl. ............... 8/589; 8/557; 8/658; 8/680; 8/914; 260/512 R; 260/512 C
[58] Field of Search ............... 8/589, 680, 557

[56] References Cited

U.S. PATENT DOCUMENTS

| | | | |
|---|---|---|---|
| 3,118,723 | 1/1964 | Harding | 8/478 |
| 4,202,838 | 5/1980 | Lauton et al. | 8/589 |
| 4,270,236 | 6/1981 | Zurbuchen et al. | 8/589 |
| 4,322,372 | 3/1982 | Wurmli et al. | 8/658 |

*Primary Examiner*—A. Lionel Clingman
*Attorney, Agent, or Firm*—Joseph G. Kolodny

[57] ABSTRACT

New condensation products of the formula

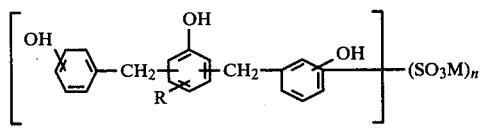

wherein R represents alkyl, cycloalkyl, aralkyl, aryl, or halogen, M represents hydrogen, an alkali metal or alkaline earth metal or an ammonium group, and n is a number from 1 to 3; these products are particularly useful as dyeing assistants for dyeing synthetic polyamide fibres with anionic dyes.

10 Claims, No Drawings

CONDENSATION PRODUCTS CONTAINING SULPHONIC ACID GROUPS: ADDITIVES FOR DYEING SYNTHETIC POLYAMIDE

This is a division of application Ser. No. 167,578 filed July 11, 1980, now U.S. Pat. No. 4,322,372 which is a continuation of application Ser. No. 937,367, filed Aug. 28, 1978, now abandoned, which is a continuation of application Ser. No. 769,376, filed Feb. 16, 1977, now abandoned, which is a continuation of application Ser. No. 659,309, filed Feb. 19, 1976, now abandoned, which is a continuation of application Ser. No. 365,886, filed June 1, 1973, now abandoned.

The invention relates to condensation products containing sulphonic acid groups, of the formula

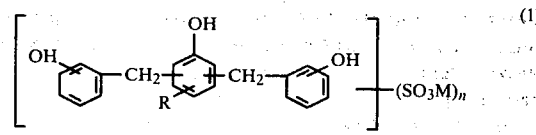

wherein R represents alkyl, cycloalkyl, aralkyl, aryl, or halogen, M represents hydrogen, an alkali metal or alkaline earth metal or an ammonium group, and n is a number from 1 to 3, to a process for their manufacture and to their use as dyeing assistants for dyeing synthetic polyamide fibre material with anionic dyes and, in particular, with 1:2 metal complex dyestuffs.

If R is alkyl, it is advantageously an alkyl group with 1 to 12, preferably 5 to 9, carbon atoms, e.g. pentyl, hexyl, n- and iso-octyl, n- and iso-nonyl, decyl or dodecyl. If R is cycloalkyl, it is advantageously a cycloalkyl group with 5 or 6 carbon atoms, e.g. cyclopentyl or cyclohexyl. As aralkyl, R represents in particular benzyl or phenylethyl. As aryl, R represents e.g. substituted benzene radicals or preferably phenyl, and as halogen, represents in particular chlorine or bromine.

Besides being hydrogen, M is an alkali metal, in particular sodium or potassium, ammonium or an ammonium group which is derived e.g. from aliphatic amines such as di- and triethylamine or mono-, di- and triethanolamine, cycloaliphatic amines, such as cyclohexylamine or heterocyclic amines, such as piperidine, morpholine, or pyridine.

The condensation products containing sulphonic acid groups according to the invention preferably correspond to the formula

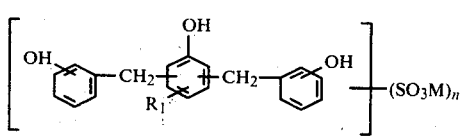

wherein $R_1$ represents alkyl with 1 to 12 carbon atoms, cycloalkyl with 5 or 6 carbon atoms, benzyl or phenylethyl, phenyl or halogen, M represents hydrogen, an alkali metal or alkaline earth metal, or an ammonium group, and n is a number from 1 to 3.

Particularly suitable condensation products containing sulphonic acid groups are those of the formula

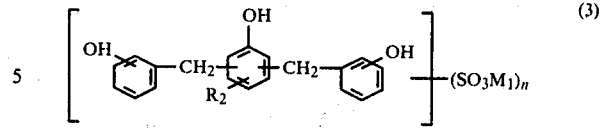

wherein $R_2$ represents alkyl with 5 to 9 carbon atoms, cyclohexyl, benzyl, phenyl, or chlorine, $M_1$ represents hydrogen, sodium, potassium, or ammonium, and n is a number from 1 to 3, or those of the formula

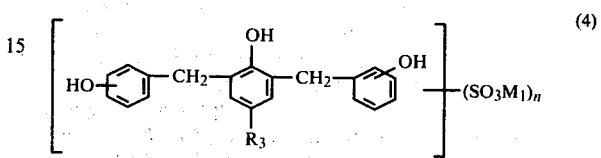

wherein $R_3$ represents alkyl with 5 to 9 carbon atoms and $M_1$ and n have the meanings given hereinbefore, or preferably those of the formula

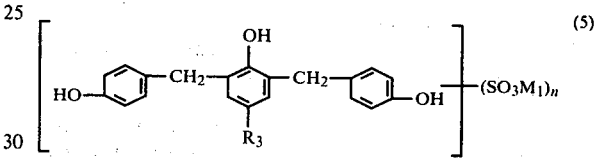

wherein $R_3$, $M_1$ and n have the meanings given hereinbefore.

To be particularly highlighted among the compounds of the formula (3) are above all the condensation products containing sulphonic acid groups of the formulae

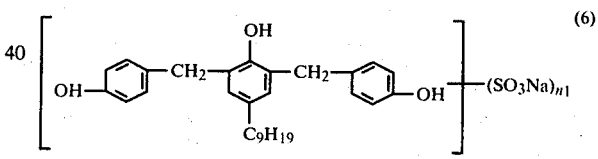

and

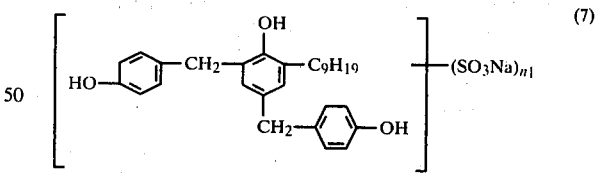

wherein $n_1$ is 1.5 to 2.5, and which as a rule are present in the form of an isomer mixture.

The condensation products containing sulphonic acid groups of the formula (1) are manufactured by (1) by reacting a dimethylol compound of the formula

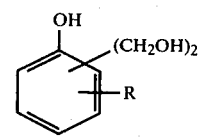

in the presence of acid catalysts with phenol in the ratio 1:2. advantageously at temperatures between 50° and 100° C., and (2) treating the resulting condensation product of the formula

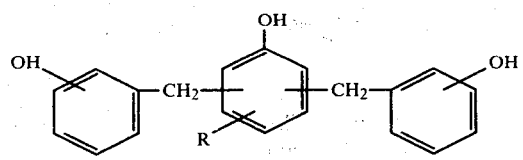

(9)

optionally in organic solvents, with sulphonating agents.

The sulphonation is performed as a rule with known sulphonating agents, for example sulphuric acid, sulphur trioxide, oleum, chlorosulphonic acid, or amidosulphonic acid. It is preferably carried out in solvents which are inert towards the cited sulphonating agents. There are used, for example, chorinated hydrocarbons, such as chloroform, carbon tetrachloride, trichloroethylene, or trichloroethane; also ethers, for example diethyl ether and dioxane. The temperature range for the sulphonation is appropriately between 0° and 100° C., preferably between 20° and 80° C. The compounds of the formula (1) contain 1 to 3, preferably 1.5 to 2.5, sulphonic acid groups.

The resulting free sulphonic acids can be converted subsequently into the corresponding alkali metal, alkaline earth metal, or ammonium salts.

The reaction of the dimethylol compounds of the formula (8) with phenol takes place in known manner, accompanied by the splitting off of water, in the presence of acid catalysts, e.g. sulphuric acid, hydrochloric acid, toluenesulphonic acid, or known Lewis acids, such as $AlCl_3$ or $BF_3$, and corresponding addition compounds. It is also possible to carry out the reactions in inert organic solvents, such as aliphatic or aromatic hydrocarbons or chlorinated hydrocarbons.

The compounds of the formulae (2) to (7) are manufactured in analogous manner. It is also possible to use mixtures of the starting phenol compounds or of the condensation products in the sulphonation reaction.

The condensation products containing sulphonic acid groups according to the invention are used as dyeing assistants for the dyeing or printing of synthetic polyamide fibre material with anionic dyes. Suitable fibre materials are those from adipic acid and hexamethylenediamine (nylon 66), from ε-caprolactam (nylon 6), from ω-aminoundecanoic acid (nylon 11), from ω-aminoenanthic acid (nylon 7), from ω-aminopelargonic acid (nylon 8), or from sebacid acid and hexamethylenediamine (nylon 610).

Optionally, it is also possible to use fibre blends with other fibre materials which do not contain poylamides. The fibre material can be in the most diverse states of processing, for example as flocks, worsted tops, yarn, wovens, blends, or also as non-wovens.

The anionic dyes are, for example, the alkali metal or ammonium salts of acid polyamide dyes or of the reactive dyes of the azo and anthraquinone series. Suitable azo dyes are preferably metal-free mono- and disazo dyes which contain one or two sulphonic acid groups, monazo, disazo and formazane dyes containing heavy metals, i.e. which contain chromium, nickel, or cobald, and, above all, metallised azo dyes which contain two molecules of azo dye bonded to a metal atom. As anthraquinone dyes there may be cited in particular sulphonated 1-amino- or 1-alkylamino-4-arylaminoanthraquinones and as reactive dyes, azo and anthraquinone dyes which contain sulpho groups and as fibre reactive group in particular an acrylic amide or α-haloacrylic amide group. As anionic dyes there are preferably used 1:2 metal complex dyes which contain as central atom a heavy metal atom, e.g. a cobalt or, in particular, a chromium atom. Linked with the central atom are two complex forming components, of which at least one is a dyestuff molecule, but preferably both are dyestuff molecules. Suitable dyestuff molecules are primarily azo dyes which in o,o′-position to the azo bridge contain one substituent which is capable of complex formation. Moreover, both dyestuff molecules involved in the complex formation can be the same or different and contain only one or more azo bridges. Examples of suitable complex forming substituents are the hydroxyl, amino, carboxyl, carbomethoxy, or methoxy group. Particularly suitable are, for example, dyes with one of the following groupings: o,o′diamino-azo, o-oxy-o′-amino-azo, o-carboxy-o′oxy-azo, o-carboxy-o′-amino-azo, o-carbomethoxy-o′-oxy-azo, o-carbomethoxy-o′-amino-azo, and, in particular, the o,o′-dioxy-azo group.

In addition to the dye and the assistant according to the invention, the dyeing preparations can contain further conventional additives, e.g. acids, salts, surface-active assistants, optionally hydrotropic agents and thickeners, these last mentioned e.g. in printing pastes and antifoaming agents.

According to the process, the dyeing preparations are as a rule acid to slightly alkaline. Advantageously they have a pH of 3 to 9, preferably 4 to 7. This acidity can be produced by adding organic or inorganic acids, for example formic, acetic, sulphuric, or phosphoric acid. But it is also possible to use potentially acid salts, e.g. ammonium sulphate.

The simultaneous use of acids and corresponding salts, e.g. acetic acid/ammonium acetate, and the buffer mixture thereby attained in the dyebaths, is advantageous.

The liquor ratios are expediently between 1:0.5 to 1:50, i.e. besides the normal liquors with ratios of 1:10 to 1:50 it is also possible to use so-called short liquors with ratios of preferably 1:0.5 to 1:5.

The amounts in which the condensation products containing sulphonic acid groups according to the invention are added to the dyebaths can vary within wide limits. Depending on the desired depth of colour, they are about 0.5 to 10% by weight, based on the weight of the dyed goods.

The dyeing of the polyamide fibre material is carried out by known methods, preferably by the exhaust method, optionally as well by the pad dyeing method or by spraying the liquor on the fibre material. The procedure is that the goods are put into the dyebath at room temperature (about 25° C.), the bath temperature is then raised to boiling temperature or to temperatures up to 130° C., whereupon dyeing is carried out over a prolonged period of time until the dyebath is almost completely exhausted.

Another suitable dyeing method consists in treating the fibre material initially for a brief time in an acid liquor which contains only the condensation products containing sulphonic acid groups. The temperature range for this preliminary treatment is about 25° to 100° C., i.e. room temperature to about the boiling temperature of the liquor. Only then, optionally after a cooling phase, is the dyestuff added to the liquor at temperature of 40° to 100° C. and dyeing is then carried out at 95° to 130° C. until the dyebath is almost completely exhausted. Optionally, the pH of the liquor can be checked after the preliminary treatment.

The condensation products containing sulphonic acid groups according to the invention are valuable dyeing assistants for dyeing fibre materials which contain polyamides. It is possible to dye these fibre materials levelly with 1:2 metal complex dyes and thereby avoid the streakiness conditioned by the material which occurs especially with polyamide fibre materials and blends.

Further advantages reside in the only slight foam development of the dyebaths which contain the condensation products containing sulphonic acid groups according to the invention, also the good water solubility and the good compatibility with further substances present in the dyebath, so that when dyeing at elevated temperature and over a prolonged period of time precipitations and undesirable deposits do not occur on fhr fibre material. The condensation products according to the invention have a stabilising action on the dyebaths, so that during the entire dyeing process these latter possess their respective full effectiveness.

The following Examples illustrate the invention, the parts and percentages being by weight unless otherwise stated.

EXAMPLES

Manufacturing Instructions 1. 220 parts of a mixture of p- and o-nonylphenol, 83 parts of water, and 178 parts of formaldehyde (37%) are mixed. While stirring thoroughly, 49 parts of sodium hydroxide solution (30%) are passed into this mixture at room temperature. The inhomogeneous mixture is slowly heated to 63° C., in the course of which at 50°–55° C. a clear solution forms. The solution is stirred for 2 hours at 63° C. The resulting dimethyl compound is isolated by acidifying with 40% sulphuric acid and separating the aqueous salt solution from the oily dimethylol compound in a separating funnel.

195 parts of melted phenol and 4 parts of concentrated hydrochloric acid (36%) are put into an agitator flask. At 40° C. the dimethylol compound is passed in with cooling, so that the temperature of the reaction mass rises to 98° C. and is kept at this temperature. Stirring is subsequently continued for 2 hours at this temperature and then the water of reaction is distilled off under vacuum. An amber coloured, brittle resin which congeals in the cold state is obtained.

The sulphonation is performed by slowly treating a solution of 83 parts of the above resin in 50 parts of carbon tetrachloride with 16 parts of chlorosulphonic acid at 30°–40° C. The reaction is terminated after 2 hours.

The reaction mixture is treated with 50 parts of water, neutralised with dilute sodium hydroxide solution (30%) and subsequently carbon tetrachloride and water are distilled off, to give 130 g of a clear, water-soluble product which consists of the compounds of the formulae (6) and (7), in which $n_1$ is 1.8. The infrared spectrum of this product shows the following bands:

| broad | bands at app. 3400 cm$^{-1}$ | strong |
| sharp | bands at app. 2950 cm | medium |
| sharp shoulder | bands at app. 2860 cm | medium |
| broad | bands at app. 1600 cm | medium |
| broad | bands at app. 1480 cm | medium-strong |
| broad shoulder | bands at app. 1435 cm | medium |
| broad | bands at app. 1370 cm | faint |
| sharp | bands at app. 1320 cm | faint |
| broad | bands at app. 1180 cm | strong |
| broad shoulder | bands at app. 1135 cm | faint |
| sharp | bands at app. 1095 cm | medium-strong |
| broad | bands at app. 1035 cm | strong |
| broad | bands at app. 915 cm | faint |
| broad | bands at app. 895 cm | faint |
| broad shoulder | bands at app. 880 cm | faint |
| broad | bands at app. 830 cm | medium |
| broad | bands at app. 795 cm | faint |
| broad | bands at app. 755 cm | faint |
| broad | bands at app. 700 cm | faint-medium |

The following homologues of the formula (10) are also manufactured in analogous manner to the described manufacturing instruction.

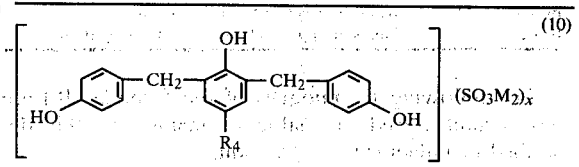

(10)

| Example | $R_4$ | $M_2$ | x |
|---|---|---|---|
| 2 | —CH$_3$ | Na | 2 |
| 3 | —C$_5$H$_{11}$ | Na | 2 |
| 4 | —C$_9$H$_{19}$ | NH$_4$ | 2 |
| 5 | —C$_{12}$H$_{25}$ | Na | 1,8 |
| 6 | —C$_9$H$_{19}$ | Na | 1,8 |
| 7 | —C$_9$H$_{19}$ | H$_2$N(CH$_3$)$_2$ | 1,8 |
| 8 | —C$_9$H$_{19}$ | HN(C$_2$H$_4$OH)$_3$ | 2,0 |
| 9 | —C$_9$H$_{19}$ | NH$_3$—⟨H⟩ | 2,5 |

EXAMPLE 10

88 parts of p-cyclohexylphenol are dissolved in 100 parts of water and 67 parts of sodium hydroxide solution (30%). To this solution are added 110 parts of formaldehyde (30%) and the mixture is heated to 50° C. While stirring, the reaction is carried out for 10 hours at this temperature. Then the reaction mixture is acidified with 40% sulphuric acid until the onset of slightly acid reaction. The dimethylol compound precipitates in the form of a fine crystal broth, which is collected by suction filtration and washed with water. The moist dimethylol compound is added by small amounts to a 50° C. warm mixture of 94 parts of phenol and 2 parts of concentrated hydrochloric acid (36%) in such a manner that the reaction temperature does not exceed 80° C. Upon completion of the addition the reaction mixture is heated to 98° C. and left to stand for 5 hours at this temperature. The resulting resin is then freed from water under vacuum. To the app. 100° C. hot resin melt are added 70 parts of dioxan. After mixing, the solution is cooled to 70° C. and diluted with 300 parts of trichloroethylene. This solution is then slowly treated at 10°–20° C. with 170 parts of chlorosulphonic acid. Sulphonation is carried out for 3 further hours at 25°–30° C., and subsequently netralisation with ammonia is effected. After the solvent has been distilled off there remains as residue a water-soluble product of the formula (10), wherein $R_4$ represents cyclohexyl, $M_2$ represents sodium, and x is 1.8.

The infrared spectrum of this product shows the following bands:

| | | |
|---|---|---|
| broad | bands at app. 3400 cm$^{-1}$ | strong |
| sharp | bands at app. 2900 cm | medium |
| sharp | bands at app. 2850 cm | faint-medium |
| broad | bands at app. 1600 cm | medium |
| broad | bands at app. 1470 cm | medium |
| sharp | bands at app. 1440 cm | faint |
| broad shoulder | bands at app. 1420 cm | faint-medium |
| broad shoulder | bands at app. 1355 cm | faint |
| broad | bands at app. 1175 cm | strong |
| broad shoulder | bands at app. 1125 cm | faint |
| sharp | bands at app. 1085 cm | medium |
| broad | bands at app. 1030 cm | medium-strong |
| broad shoulder | bands at app. 960 cm | faint |
| broad | bands at app. 920 cm | faint |
| broad | bands at app. 890 cm | faint |
| broad | bands at app. 865 cm | faint |
| broad | bands at app. 825 cm | faint |
| broad | bands at app. 790 cm | faint |
| broad | bands at app. 765 cm | faint |
| broad | bands at app. 700 cm | faint-medium |

The following homologues of the formula (10) are also manufactured in analogous manner to this described manufacturing instruction:

| Example | R$_4$ | M$_2$ | x |
|---|---|---|---|
| 11 | —C$_6$H$_5$ | Na | 1,8 |
| 12 | —C$_6$H$_{11}$ | K | 2 |
| 13 | —CH$_2$—C$_6$H$_5$ | Na | 1,8 |
| 14 | —Cl | Na | 2,1 |
| 15 | —Cl | K | 1,5 |

Application Examples

EXAMPLE 16

A nylon 66 fabric is put, in the liquor ratio 1:40 into a dyebath of 25° C. which contains 0.25 g/l of ammonium acetate and 1.5% of the condensation product according to Manufacturing Instruction 1 and which is adjusted with acetic acid (80%) to pH 4. The liquor is then heated within 30 minutes to 98° C. and treatment is effected for 15 minutes at this temperature. The liquor is cooled to 60° C. and 1.8% of the chromium complex of the dye of the formula

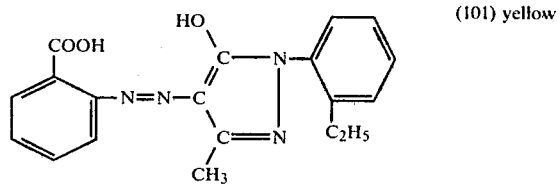

(101) yellow is added thereto. The liquor is again heated within 30 minutes to 89° C. and dyeing is then carried out at this temperature for 60 minutes. The goods are then rinsed and dried. A level, non-streaky dyeing is obtained.

EXAMPLE 17

A nylon 6 fabric is put in the liquor ratio 1:40 into a dyebath of 25° C. which contains 0.25 g/l of ammonium acetate, 2,5% of the condensation product according to Manufacturing Instruction 1 and 2.2% of the 1:2 chromium complex of the dye of the formula

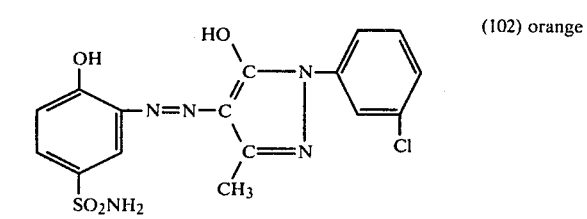

(102) orange and which is adjusted with acetic acid to pH 5. The liquor is then heated within 30 minutes to 98° C. and dyeing is carried out for 1 hour at this temperature. After the liquor has cooled, the goods are rinsed and dried to give a non-streacky orange dyeing with good fastness properties.

Suitable dyes are also the 1:2 chromium complex of the dye of the formula

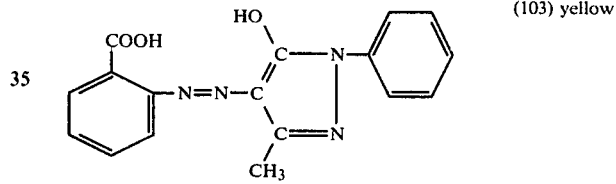

(103) yellow the 1:2 chromium complex of the dye of the formula

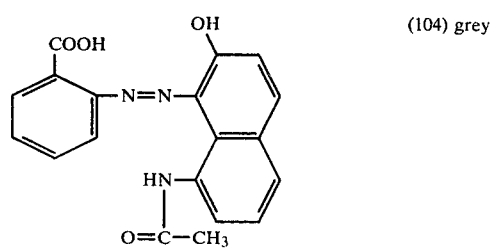

(104) grey the 1:2 cobalt complex of the dye of the formula

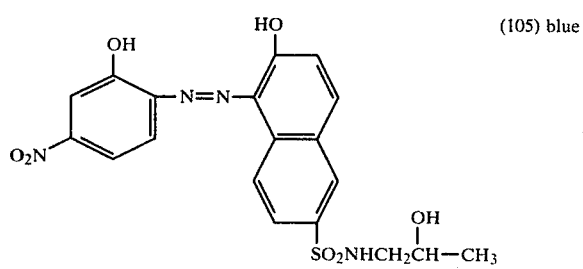

(105) blue the 1:2 cobald complex of the dys of the formula

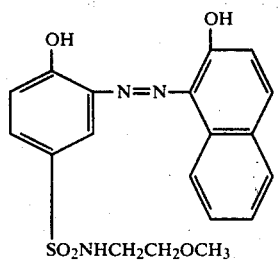

(106) dark purplish red the 1:2 chromium complex of the dye of the formula

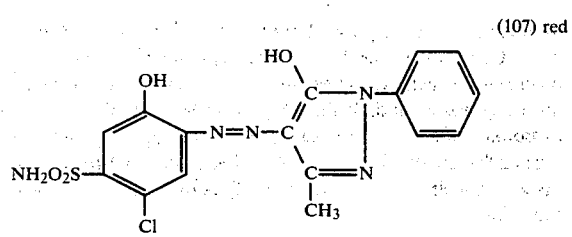

(107) red the 1:2 chromium complex of the dye of the formula

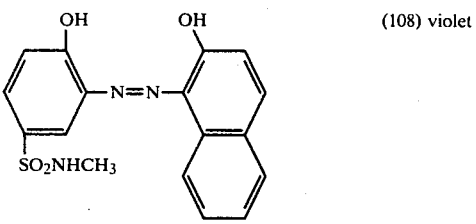

(108) violet

EXAMPLE 18

A nylon 66 knitted fabric is put in the liquor ratio 1:5 into a dyebath of 25° C. which contains 1 ml/l of 80% acetic acid, 2 g/l of the condensation product according to Manufacturing Instruction 1, and 0.6% of the 1:2 chromium complex of the dye of the formula

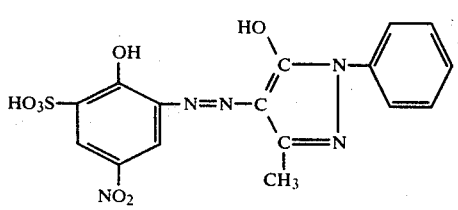

(109)

The liquor is then heated within 20 minutes to 98° C. and dyeing is carried out for 60 minutes at this temperature. After the liquor has cooled, the goods are rinsed and dried to give a non-streaky red dyeing.

EXAMPLE 19

The following printing paste is manufactured: 1.2 parts of the 1:2 chromium complex of the dye of the formula

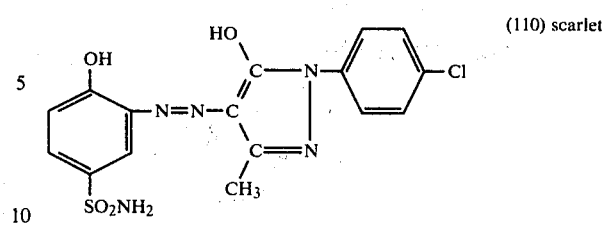

(110) scarlet 25 parts of thiodiethylene glycol
25 parts of urea
500 parts of a 12% aqueous locust bean meal thickening
30 parts of ammonium tartrate solution (20%)
5 parts of silicone antifoaming agent (5% solution in 2-ethylhexanol (1))
10 parts of the condensation product according to Manufacturing Instruction 1, made up to 1000 parts with water.

A screen printing is prepared in the conventional manner with this paste on nylon 66 jersey material. The printed material is then fixed by steaming in a star for 20 minutes at 0.15 atmosphere absolute pressure, then rinsed cold and subsequently at 60° C. with water.

The resulting bright red screen printing is distinguished by good levelness and the distinctness of the print is also retained.

EXAMPLE 20

A nylon 66 fabric is put in a liquor ratio of 1:40 into a dyebath of 40° C. which contains 3% of ammonium acetate and 2% of the condensation product according to Manufacturing Instruction 1 (both percentages being based on the weight of the fabric), and which is adjusted with 80% acetic acid to pH 6. The bath is then kept for 10 minutes at 40° C. and 0.22% of the dye of the formula

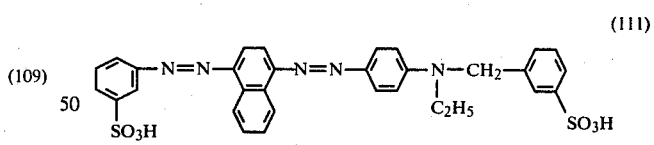

(111)

is added. After a further 10 minutes the temperature of the bath is raised within 30 minutes to 98° C. and dyeing is carried out for 60 minutes at this temperature. After the liquor has cooled the dyeing is rinsed and dried. A level, non-streaky dark purplish red dyeing is obtained.

EXAMPLE 21

Nylon jersey fabric is put in a liquor ratio of 1:40 into a dyebath of 40° C. which contain 3% of ammonium acetate and 0.5% of the condensation product according to Manufacturing Instruction 1. The bath is subsequently kept for 10 minutes at 40° C. and 0.8% of the dye of the formula

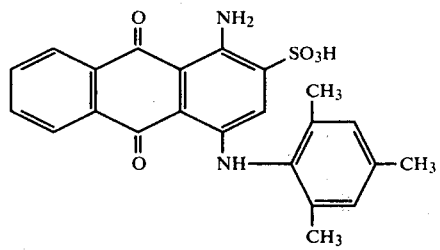
(112)

in the customary preparation is added to the bath. After a further 10 minutes at 40° C. the temperature of the bath is raised within 30 minutes to 98° C. and dyeing is carried put for 1 hour at this temperature. After the bath has cooled, the dyeing is rinsed and dried. A level, non-streaky, blue dyeing is obtained.

EXAMPLE 22

A nylon 66 knitted fabric is put in the liquor ratio of 1:40 into a bath of 25° C. which contains 0.25 g/l of ammonium acetate and 2% of the condensation product according to Manufacturing Instruction 1, based on the weight of the fabric, and which is adjusted with 80% acetic acid to pH 4. The dyebath is then heated within 30 minutes to 98° C. and kept for 15 minutes at this temperature. It is then cooled to 60° C. and 1% of the dye of the formula

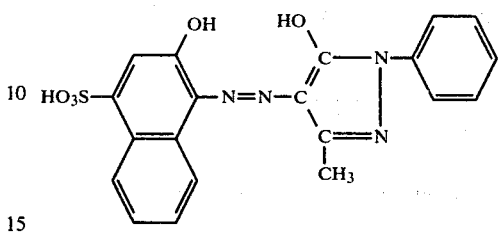
(113)
1:1-Cr-complex is added to the liquor. This is again heated within 30 minutes to 98° C. and then dyeing is carried out for 60 minutes at this temperature. The material is subsequently rinsed and dried. A non-streaky pink dyeing is obtained. Further non-streaky, level dyeings are obtained by substituting for 1% of the dye of the formula given therein Y% of one of the dyes listed in the following Table.

| Example | Dye | Y % | Shade |
|---|---|---|---|
| 23 | ![structure] 1:2 Cr—complex | 0,5% | blue |
| 24 | ![structure] | 0,5% | orange |

-continued
| Example | Dye | Y % | Shade |
|---|---|---|---|
| 25 | 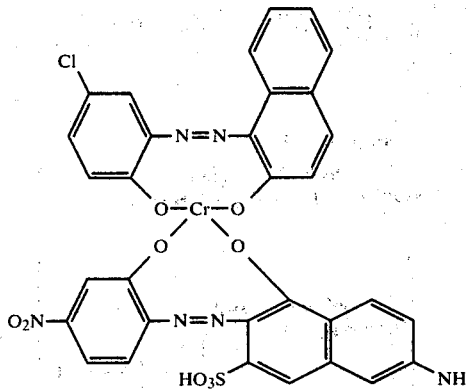 | 1,0% | grey |
| 26 | 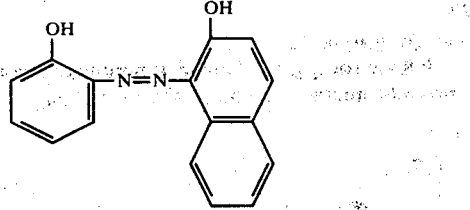 1:2-cobalt complex | 0,5% | red |
| 27 | 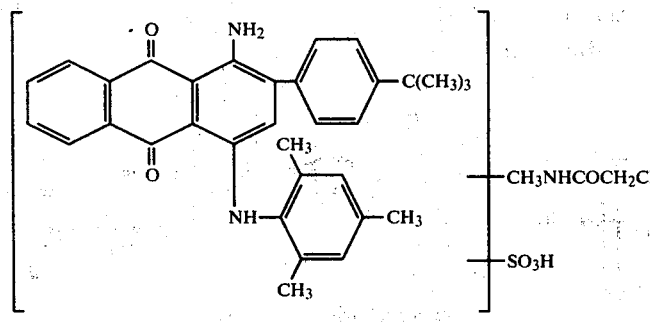 | 0,5% | violet |
| 28 | 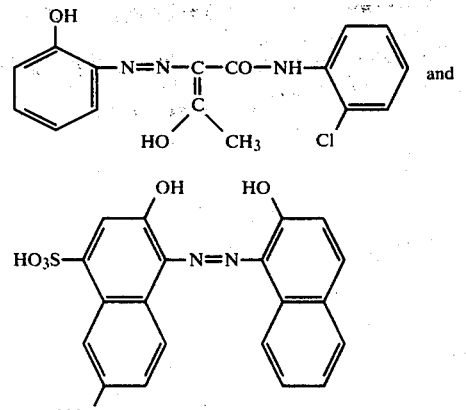 and chromium mixed complex | 0,5% | olive |
We claim:
1. A process for dyeing synthetic polyamide fibres with anionic dyes, wherein the dyeing preparations contain a condensation product of the formula
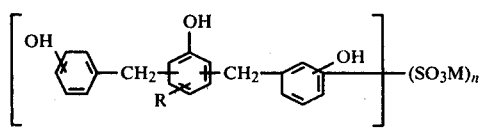

wherein R represents alkyl, cycloalkyl, aralkyl, aryl or halogen, M represents hydrogen, an alkali metal or alkaline earth metal, or an ammonium group, and n is a number from 1 to 3.

2. A process of claim 1 wherein, in the condensation product, R represents alkyl with 1 to 12 carbon atoms, cycloalkyl with 5 or 6 carbon atoms, benzyl, phenylethyl, phenyl, or halogen.

3. A process of claim 1 wherein, in the condensation product R represents alkyl with 5 to 9 carbon atoms, cyclohexyl, benzyl, phenyl, or chlorine, M represents hydrogen, sodium, potassium, or ammonium, and n is a number from 1 to 3.

4. A process of claim 3 where said condensation product is one of the formula

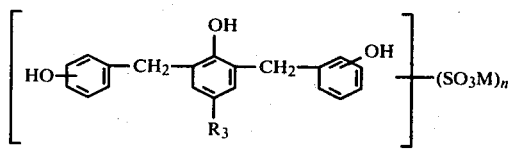

wherein $R_3$ represents alkyl with 5 to 9 carbon atoms and M and n have the meanings given in claim 3.

5. A process of claim 4 wherein the condensation product is one of the formula

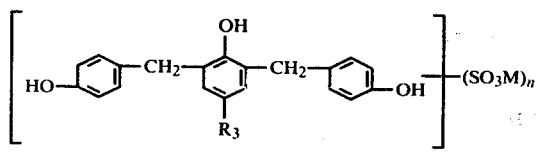

wherein $R_3$, M, and n have the meanings given in claim 4.

6. A process of claim 5 wherein the condensation product is one of the formula

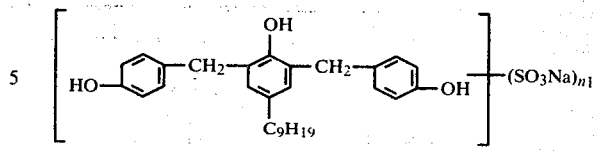

wherein $n_1$ is 1.5 to 2.5.

7. A process of claim 5 wherein the condensation product is one of the formula

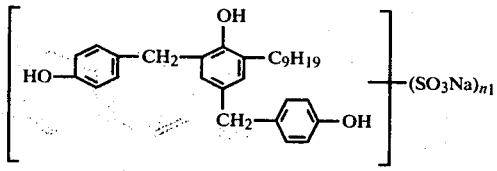

wherein $n_1$ is 1.5 to 2.5.

8. A process of claim 3 wherein the condensation product mixture, is one of the formulae

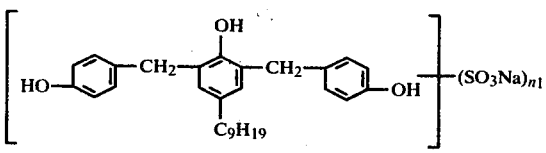

and

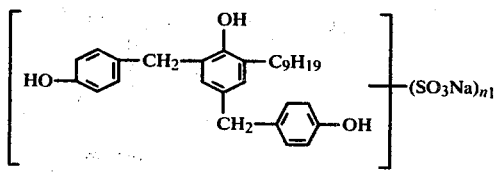

wherein $n_1$ is 1.5 to 2.5.

9. A process of claim 8 wherein, in the condensation product mixture, $n_1$ is 1.8.

10. Synthetic polyamide fibres which are dyed by the process according to claim 1.

* * * * *